United States Patent [19]
Racz

[11] Patent Number: 5,722,955
[45] Date of Patent: Mar. 3, 1998

[54] PRESSURE SENSING SYRINGE

[75] Inventor: Gabor J. Racz, Lubbock, Tex.

[73] Assignee: Epimed International, Inc., Lubbock, Tex.

[21] Appl. No.: 634,681

[22] Filed: Apr. 18, 1996

Related U.S. Application Data

[63] Continuation of Ser. No. 285,841, Aug. 4, 1994, abandoned.

[51] Int. Cl.$^6$ .................................................. A61M 1/00
[52] U.S. Cl. ..................................... 604/121; 604/218
[58] Field of Search ......................... 604/121, 124, 604/152, 155, 207, 218, 229, 227, 214

[56] References Cited

U.S. PATENT DOCUMENTS

| | | | |
|---|---|---|---|
| 1,863,785 | 6/1932 | Dickinson | 604/207 |
| 3,623,474 | 11/1971 | Heilman . | |
| 3,744,316 | 7/1973 | Kuzyk . | |
| 3,756,390 | 9/1973 | Abbey et al. | 604/87 |
| 3,998,223 | 12/1976 | Dawe . | |
| 4,000,741 | 1/1977 | Binard et al. . | |
| 4,030,498 | 6/1977 | Tompkins | 604/152 |
| 4,064,879 | 12/1977 | Leibinsohn . | |
| 4,074,714 | 2/1978 | Binard et al. | 604/121 |
| 4,275,730 | 6/1981 | Hussein . | |
| 4,324,235 | 4/1982 | Beran . | |
| 4,329,985 | 5/1982 | Bonchek . | |
| 4,370,982 | 2/1983 | Reilly . | |
| 4,384,470 | 5/1983 | Fiore . | |
| 4,624,659 | 11/1986 | Goldberg et al. . | |
| 4,723,556 | 2/1988 | Sussman . | |
| 4,755,172 | 7/1988 | Baldwin . | |
| 4,759,750 | 7/1988 | DeVries et al. . | |
| 4,815,313 | 3/1989 | Beard . | |
| 4,817,629 | 4/1989 | Davis et al. . | |
| 4,863,429 | 9/1989 | Baldwin . | |
| 4,929,238 | 5/1990 | Baum . | |
| 5,009,662 | 4/1991 | Wallace et al. . | |
| 5,019,041 | 5/1991 | Robinson et al. . | |
| 5,047,015 | 9/1991 | Foote et al. . | |
| 5,118,907 | 6/1992 | Stout et al. . | |
| 5,135,488 | 8/1992 | Foote et al. . | |
| 5,147,300 | 9/1992 | Robinson et al. . | |
| 5,168,757 | 12/1992 | Rabenau et al. . | |
| 5,171,299 | 12/1992 | Heitzmann et al. . | |
| 5,215,523 | 6/1993 | Williams et al. . | |
| 5,270,685 | 12/1993 | Hagen et al. . | |

*Primary Examiner*—Michael Buiz
*Assistant Examiner*—Nguyen At
*Attorney, Agent, or Firm*—Trask, Britt & Rossa

[57] ABSTRACT

A pressure sensing syringe comprising a syringe barrel, a syringe piston and a compressible material.

6 Claims, 2 Drawing Sheets

PRESSURE SENSING SYRINGE

This application is a continuation of application Ser. No. 08/285,841, filed Aug. 4, 1994, now abandoned.

BACKGROUND OF THE INVENTION

1. Field of the Invention

This invention relates to hypodermic syringes with pressure sensing capabilities.

2. State of the Art

Syringes are commonly used by a wide variety of personnel for many medical purposes. For instance, syringes are used to pump liquid into a body cavity of a patient particularly in situations where it is desired to limit the pressure of the fluid to a predetermined amount. In spinal anesthesia procedures, an anesthetic solution is pumped from a syringe through a needle into the epidural, subdural, and subarachnoid space, an inelastic pouch, thereby requiring careful attention to the volume of the solution and the pressure of the solution. In other instances, it is desired to be able to have an indication of the pressure level of a blood vessel or a body cavity, such as if the needle of a syringe pierces an artery.

Attempts have been made at developing syringes which have pressure limiting, dampening, or indicating features. One prior art syringe uses a flexible diaphragm to cover a cavity formed in the plunger to provide a more uniform injection pressure. Another prior art syringe uses either a flexible diaphragm to cover a cavity of the plunger, an expanding plug on the plunger end or inflatable balloons on the exterior of the plunger barrel. Yet another prior art syringe uses either a spring loaded cylinder and corrugated plug on the end of the plunger, a bellows on the end of the plunger or spring loaded bellows on the end of the plunger. Such prior art devices are illustrated in U.S. Pat. Nos. 3,998,223, 4,000,741, 4,064,879, 4,329,985 and 4,624,659.

Yet other types of pressure sensing syringes which use either a fluid bypass arrangement, tactile indicator or alarm indicator are illustrated in U.S. Pat. Nos. 4,275,730, 4,759,750 and 5,270,685.

Still other types of pressure sensing devices used in medical procedures are illustrated in U.S. Pat. Nos. 3,623,474, 3,744,316, 4,324,235, 4,370,982, 4,384,470, 4,723,556, 4,755,172, 4,815,313, 4,817,629, 4,863,429, 4,929,238, 5,009,662, 5,019,041, 5,047,015, 5,118,907, 5,147,300, 5,135,488, 5,168,757, 5,171,299 and 5,215,523.

While such syringes or devices offer ways of sensing pressure, an effective, simple means is needed to detect pressure changes when using a syringe which allows the easy detection of small changes of pressure, both increases and decreases. Also, the syringe should minimize the risk of injecting air into a body cavity or blood vessel from any air escaping from the pressure sensing mechanism of the syringe. The syringe should be easily fabricated and inexpensive.

BRIEF SUMMARY OF THE INVENTION

The present invention relates to a hypodermic syringe with pressure sensing capabilities. The syringe comprises a barrel, a plunger and pressure sensing member contained within the barrel or in the plunger. The pressure sensing member may have corrugations thereon. The corrugations may be colored or have colored elastomeric members thereon.

The present invention will be better understood when the drawings are taken in conjunction with the detailed description of the invention.

DETAILED DESCRIPTION OF THE ILLUSTRATED EMBODIMENT

Figure 1:
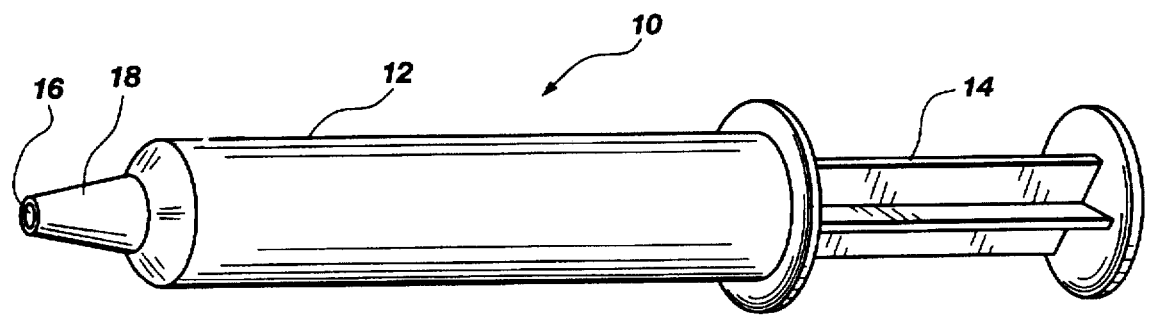
FIG. 1 is a drawing of a syringe embodying the present invention.

Referring to drawing FIG. 1, a syringe 10 of the present invention is shown. The syringe 10 comprises a barrel 12 and plunger 14. The syringe 10 can be and is of various sizes, lengths and proportions. The barrel 12 can be made of any suitable material, such as glass or translucent or transparent plastic. The inner wall or bore of the barrel is smooth to provide a leak proof slidable seal with a portion of the plunger. The plunger 14 having an elastomeric seal thereon (not shown) forces any fluid in the barrel 12 through aperture 16 and any needle (not shown) connected to the end 18 of the barrel 12.

Figure 2:
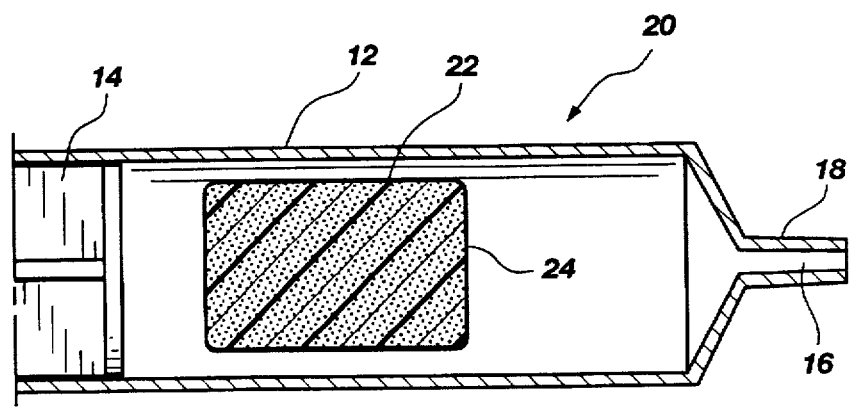
FIG. 2 is a cross-sectional view of a portion of a syringe illustrating a first embodiment of the present invention.

Referring to drawing FIG. 2, a first embodiment 20 of the present invention is shown. The syringe barrel 12 contains an elongated circular member 22 of suitable compressible material, such as an open cell foam including a plurality of open cells, having an inert impermeable coating 24 thereon to prevent fluid from permeating or being absorbed by the compressible material 22. When the barrel 12 is filled with fluid as the fluid pressure in the barrel 12 changes, the compressible material will react to any such pressure changes by increasing in size or decreasing in size with such changes being visibly enhanced by the magnification effect of the fluid in the barrel. Since the compressible material 22 may be observed through the barrel 12, any fluid pressure change may be readily observed by a user of the syringe to indicate a lower fluid pressure or a higher fluid pressure, such as an artery. The coating 24 on the compressible material 22 may be of any suitable type such as mylar or polyethylene.

As shown, the compressible material 22 having coating 24 thereon is free to float within the barrel 12 at any position therein.

Figure 3:
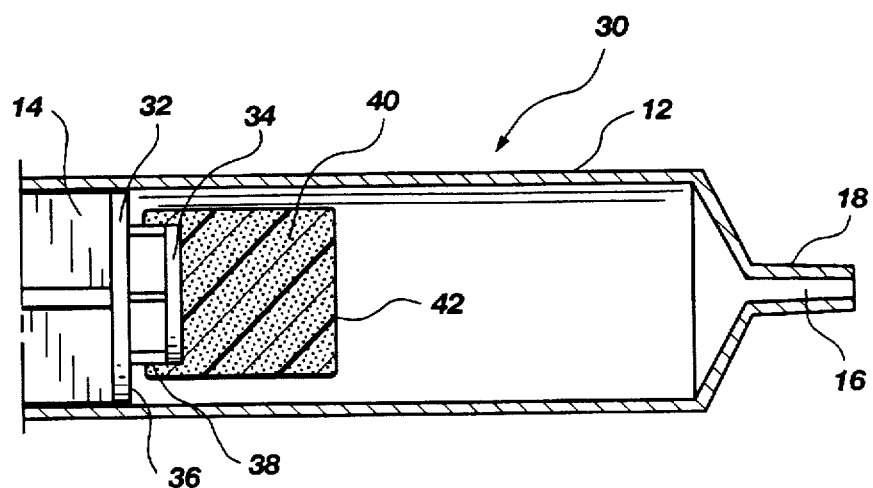
FIG. 3 is a cross-sectional view of a portion of a syringe illustrating a second embodiment of the present invention.

Referring to drawing FIG. 3, a second embodiment 30 of the present invention is shown. The syringe barrel 12 is similar to that described hereinbefore. The plunger 14 comprises an elongate cylindrical member having piston 32 formed on one end thereof. The piston 34 may include an annular elastomeric seal member thereon to sealingly engage the bore or interior of the barrel 12. The piston 32 includes circular disc 34 on one side 36 thereof connected to the piston 32 by members 38.

Secured to disc 34 is compressible member 40 formed of any suitable compressible material, such as open cell foam, having inert impermeable coating 42 thereon. The member 40 may be secured to the disc 34 by any suitable means, such as an annular rib surrounding the circumference of the disc 34, by adhesive, etc. By securing the member 40 to the plunger 14 the member's 40 location is readily determined within the barrel for easy visual reference.

Figure 4:
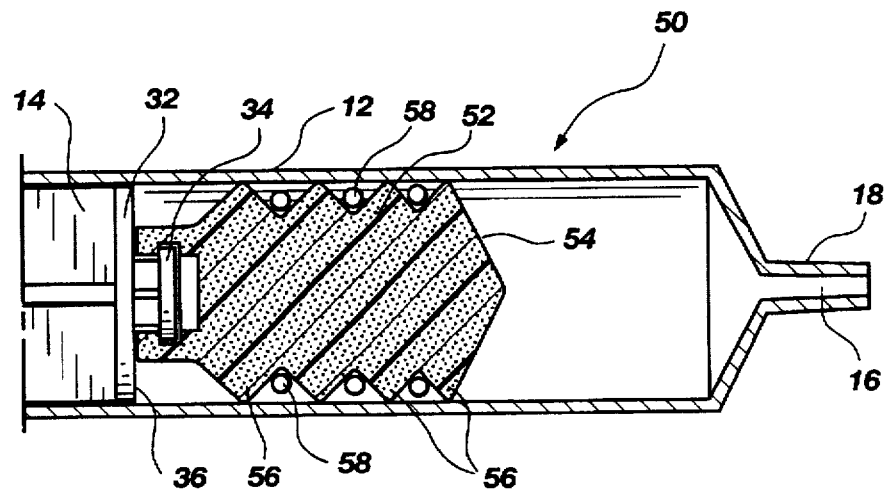
FIG. 4 is a cross-sectional view of a portion of a syringe illustrating a third embodiment of the present invention.

Referring to drawing FIG. 4, the third embodiment 50 of the present invention is shown. The barrel 12 is similar to that described hereinbefore. The plunger 14 is similar to that described with respect to the previous embodiment 30 of the present invention. The compressible member 52 comprises an elongated cylindrical member of suitable compressible material, such as open cell foam, having an inert impermeable coating 54 thereon and having one or more corrugations 56 on the exterior thereof engaging the interior or bore of the barrel 12. The corrugations 56 may be formed of different color material than that of member 52, if desired. Alternately, colored annular elastomeric members 58 may be included on member 52 between adjacent corrugations 56, if desired.

During fluid pressure changes in the barrel 12, the compressible member 52 will expand or compress accordingly. At such time, the corrugations 56 may be readily observed through the barrel 12. If the corrugations 56 are colored, any compression or expansion of the member 52 will cause the colored corrugations 56 to be readily visible through the barrel 12 or their visibility to be diminished. Similarly, if the compressible member 52 contains colored elastomeric members 58 in the corrugations 56, any compression or expansion of the member 52 will cause the members 58 to be readily visible or have their visibility diminished.

Figure 5:
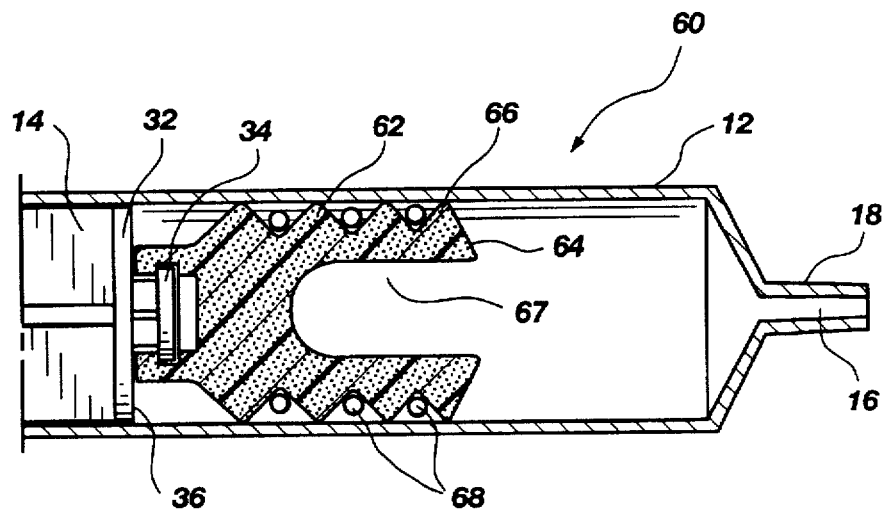
FIG. 5 is a cross-sectional view of a portion of a syringe illustrating a fourth embodiment of the present invention.

Referring to drawing FIG. 5, a fourth embodiment 60 of the present invention is shown. The barrel 12 is similar to that described hereinbefore. The plunger 14 is similar to that described with respect to the previous embodiments 30 and 50 of the present invention. The compressible member 62 comprises an elongated cylindrical member of suitable compressible material, such as open cell foam, having an inert impermeable coating 64 thereon, having one or more corrugations 66 on the exterior thereof engaging the interior or bore of the barrel 12 and having a cavity 67 formed thereon. The corrugations 66 may be formed of different color material than that of member 62, if desired. Alternately, colored annular elastomeric members 68 may be included on member 62 between adjacent corrugations 66, if desired. Again, during fluid pressure changes in the barrel 12 the compressible member 62 will expand or compress accordingly. At such time, the corrugations 66 may be readily observed through the barrel 12. If the corrugations are colored, any compression or expansion of the member 62 will cause the colored corrugations 66 to be readily visible through the barrel 12 or their visibility to be changed. Additionally, fluid pressure acting on compressible member 62 via cavity 67 will cause some of the corrugations 66 either to be compressed into the bore of barrel 12 or slightly disengaged from the bore of the barrel 12 thereby increasing or decreasing the friction of the member 62 with respect to the barrel 12. As previously described, during fluid pressure changes in the barrel 12 the compressible member 62 having elastomeric members 68 thereon will expand or compress accordingly causing visibility changes with respect to the members 68.

Figure 6:
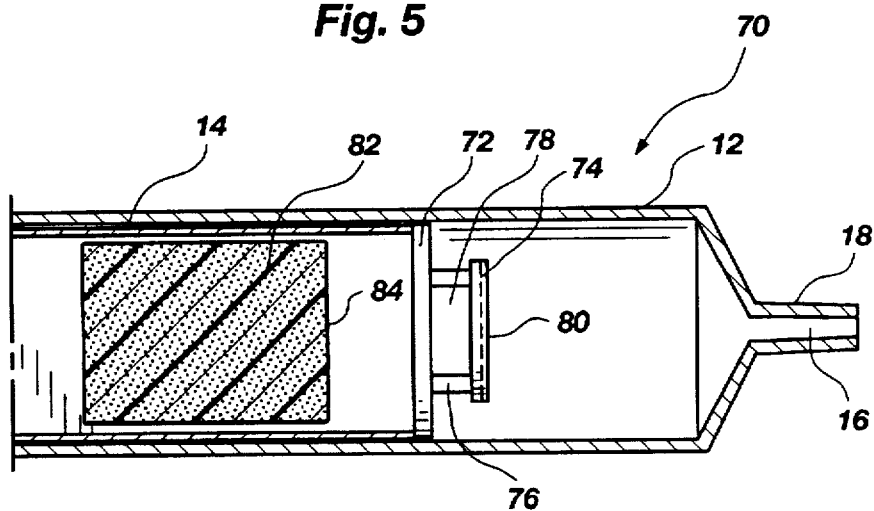
FIG. 6 is a cross-sectional view of a portion of a syringe illustrating a fifth embodiment of the present invention.

Referring to drawing FIG. 6, a fifth embodiment 70 of the present invention is shown. The barrel 12 is similar to that described hereinbefore. The plunger 14 comprises an elongated hollow cylindrical member having piston 72 formed on one end thereof. The piston 72 may include an annular elastomeric seal member thereon to sealingly engage the bore or interior of the barrel 12. The piston 72 includes circular disc 74 on one side thereof connected to piston 72 via annular portion 76 having aperture 78 therethrough and elastomeric flexible diaphragm 80 resiliently sealingly secured to disc 74 covering aperture 78. Contained within plunger 14 is compressible member 82 formed of any suitable compressible material, such as open cell foam, having inert impermeable coating 84 thereon. The interior of the plunger 14 is fried with a suitable fluid, such as a saline solution. Any fluid pressure changes in the barrel 12 will be communicated via flexible diaphragm 80 through the fluid filling the interior of plunger 14 to cause the compression or expansion of the compressible member 82 which will be visible through the plunger 14 wall and barrel wall. In this manner, the volume and pressure level of the fluid in the barrel 12 may be easily controlled and monitored.

As can be seen from the foregoing, the syringe of the present invention offers advantages over the prior art. As the compressible member has an inert impermeable coating thereon no air is displaced from the compressible member which might be injected into a patient. The compressible member may be made of any easily compressible material. Also, the compressible member may be installed in the syringe barrel as an independent member, secured to the piston in the syringe barrel or installed in a hollow fluid-filled piston used in the syringe barrel with fluid pressure therein being transmitted via a diaphragm to the compressible member. The syringe is easily manufactured from a variety of materials, such as glass and plastics.

What is claimed is:

1. A pressure sensing syringe, said syringe having a syringe barrel having an open end and a closed end with an aperture therethrough, syringe piston, and pressure responsive member located in said syringe barrel capable of indicating the change of pressure of a fluid in said syringe during the injection of said fluid into a patient, said syringe comprising:

a syringe barrel having a portion thereof being translucent to observe the interior of the syringe barrel;

a syringe piston sealingly slidingly engaging the interior of the syringe barrel; and a pressure responsive member located in the syringe barrel in the portion of the syringe barrel between the syringe piston and the closed end of the syringe barrel, the pressure responsive member including:

a compressible material including open cell foam having a plurality of open cells therein, and an impermeable coating on the compressible material to prevent said fluid from permeating the compressible material or being absorbed by the compressible material, the compressible material being visible through the translucent portion of the syringe barrel for indicating said change of pressure of said fluid in the syringe barrel during said injection of said fluid wherein the compressible material is retained within said syringe barrel by said syringe piston.

2. The syringe of claim 1 wherein:

the compressible material is retained within said syringe barrel having a portion of the compressible material secured to a portion of said syringe piston and having an area of clearance formed between the compressible material and said syringe barrel to prevent the compressible material from contacting said syringe barrel during said injection of said fluid.

3. The syringe of claim 1 wherein:

the compressible material is retained within said syringe barrel having a portion of the compressible material secured to a portion of said syringe piston, the compressible material having at least one corrugation formed on the exterior thereof, the compressible material having an area of clearance formed between the compressible material and said syringe barrel to prevent the compressible material from contacting said syringe barrel during said injection of said fluid.

4. The syringe of claim 3 wherein:

the corrugation on the exterior of the compressible material has another readily visible color differing from said color of the compressible material to indicate said change of pressure of said fluid in said syringe during said injection.

5. The syringe of claim 3 wherein:

an elastomeric member is installed on the exterior of the compressible member, the elastomeric member having a color differing from that of the compressible member to indicate said change of pressure of said fluid in said syringe during said injection.

6. The syringe of claim 3 wherein:

the compressible member having a cavity formed in one end thereof for transmitting said pressure within the syringe barrel to the compressible member to indicate said change of pressure of said fluid in said syringe during said injection.

* * * * *

UNITED STATES PATENT AND TRADEMARK OFFICE
CERTIFICATE OF CORRECTION

PATENT NO. : 5,722,955
DATED : March 3, 1998
INVENTOR(S) : Racz

It is certified that error appears in the above-identified patent and that said Letters Patent is hereby corrected as shown below:

Column 2 line 32, after "member" delete "22";
Column 2, line 33, after "material" insert --22--;
Column 2, line 38, after "material" insert --22--;
Column 2, line 55, change "34" to --32--;
Column 3, line 35, change "thereon" to --therein--.
Column 4, line 30, after "indicating" change "the" to --a--;
Column 4, line 34, after "observe" change "the" to --an--;
Column 4, line 38, after "barrel in" change "the" to --a--;
Column 4, line 49, after "syringe" delete "barrel";
Column 5, line 6, change "another" to --a--;
Column 5, lines 6-7, change "said color" to --the color--; and
Column 6, line 7, after "syringe" delete "barrel".

Signed and Sealed this

Tenth Day of August, 1999

Attest:

Q. TODD DICKINSON

*Attesting Officer*            *Acting Commissioner of Patents and Trademarks*